United States Patent
Li et al.

(10) Patent No.: US 12,280,426 B2
(45) Date of Patent: Apr. 22, 2025

(54) Si-CONTAINING HIGH-STRENGTH AND LOW-MODULUS MEDICAL TITANIUM ALLOY, AND ADDITIVE MANUFACTURING METHOD AND USE THEREOF

(71) Applicants: South China University of Technology, Guangzhou (CN); Huazhong University of Technology, Wuhan (CN); Jilin University, Changchun (CN)

(72) Inventors: Yuanyuan Li, Guangzhou (CN); Chao Yang, Guangzhou (CN); Xuan Luo, Guangzhou (CN); Dongdong Li, Changchun (CN); Yanguo Qin, Changchun (CN); Ning Li, Wuhan (CN)

(73) Assignee: South China University of Technology, Guangzhou (CN)

( * ) Notice: Subject to any disclaimer, the term of this patent is extended or adjusted under 35 U.S.C. 154(b) by 113 days.

(21) Appl. No.: 17/768,925

(22) PCT Filed: Oct. 29, 2020

(86) PCT No.: PCT/CN2020/124598
§ 371 (c)(1),
(2) Date: Apr. 14, 2022

(87) PCT Pub. No.: WO2021/139334
PCT Pub. Date: Jul. 15, 2021

(65) Prior Publication Data
US 2024/0100598 A1 Mar. 28, 2024

(30) Foreign Application Priority Data
Jan. 6, 2020 (CN) .......................... 202010009147.2

(51) Int. Cl.
*B22F 10/28* (2021.01)
*B22F 9/08* (2006.01)
(Continued)

(52) U.S. Cl.
CPC ................ *B22F 10/28* (2021.01); *B22F 9/08* (2013.01); *B22F 10/36* (2021.01); *B22F 10/366* (2021.01);
(Continued)

(58) Field of Classification Search
CPC ........ B22F 10/28; B22F 12/17; B22F 10/366; B22F 9/08; B22F 10/32; B22F 10/38; B22F 2009/0808; B22F 2301/205
See application file for complete search history.

(56) References Cited

FOREIGN PATENT DOCUMENTS

| CN | 101899592 A | 12/2010 | |
|---|---|---|---|
| CN | 104263996 A * | 7/2015 | ............. A61L 27/06 |

(Continued)

OTHER PUBLICATIONS

CN104263996A English (Year: 2015).*
(Continued)

*Primary Examiner* — Ricardo D Morales
(74) *Attorney, Agent, or Firm* — The Dobrusin Law Firm, PC

(57) ABSTRACT

The present invention relates to a Si-containing high-strength and low-modulus medical titanium alloy, and an additive manufacturing method and use thereof. The additive manufacturing method comprises alloy ingredient design, powder preparation, model construction and substrate preheating, and additive manufacturing molding; wherein the Si-containing high-strength and low-modulus medical titanium alloy is designed in the ingredient proportion of Ti 60-70 at. %, Nb 16-24 at. %, Zr 4-14 at. %, Ta 1-8 at. %, Si 0.1-5 at. %. The principle of the present invention
(Continued)

is design of a medical β-type titanium alloy having high-strength and low-modulus and good biocompatibility by using d-electron theory; reducing the difference of thermal expansion between the silicide and the β-Ti phase by pre-heating, and at the same time, ensuring that there is a sufficient degree of cooling in the additive manufacturing process to promote the transition of the alloy from the divorced eutectic reaction to the precipitation reaction, thereby solving the common problems, such as the deterioration of mechanical properties caused by the continuous distribution of the Si-containing phase along the grain boundary and the cracking caused by the difference of thermal expansion coefficient between different phases.

14 Claims, 1 Drawing Sheet

(51) Int. Cl.
*B22F 10/32* (2021.01)
*B22F 10/36* (2021.01)
*B22F 10/366* (2021.01)
*B22F 10/38* (2021.01)
*B22F 12/17* (2021.01)

(52) U.S. Cl.
CPC ...... *B22F 12/17* (2021.01); *B22F 2009/0808* (2013.01); *B22F 10/32* (2021.01); *B22F 10/38* (2021.01); *B22F 2301/205* (2013.01)

(56) References Cited

FOREIGN PATENT DOCUMENTS

| CN | 106312060 A | 1/2017 |
|---|---|---|
| CN | 107034383 A | 8/2017 |
| CN | 109332698 A | 2/2019 |
| CN | 109926582 A | 6/2019 |
| CN | 111118339 A | 5/2020 |
| WO | 2017/048199 A1 | 3/2017 |

OTHER PUBLICATIONS

Guo et al Study of Bone Regeneration and Osteointegration Effect of a Novel Selective Laser-Melted Titanium-Tantalum-Niobium-Zirconium Alloy Scaffold (Year: 2019).*

Mehjabeen Redefining the b-Phase Stability in Ti—Nb—Zr Alloys for Alloy Design and Microstructural Prediction (Year: 2018).*

Chinese Doctoral Dissertations Full-Text Database, Engineering Science and Technology dated Feb. 15, 2017.

International Search Report dated Feb. 1, 2021, Application No. PCT/CN2020/124598.

* cited by examiner

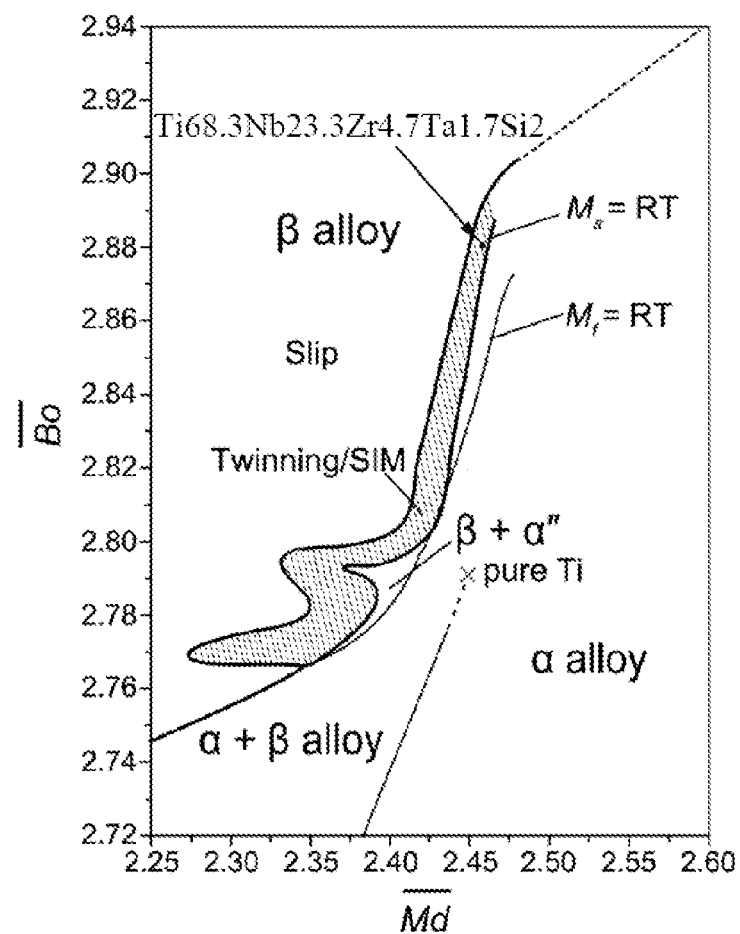

Si-CONTAINING HIGH-STRENGTH AND LOW-MODULUS MEDICAL TITANIUM ALLOY, AND ADDITIVE MANUFACTURING METHOD AND USE THEREOF

TECHNICAL FIELD

The present invention relates to the fields of titanium alloy materials and additive manufacturing technologies, and in particular, to an additive manufacturing method of a high-strength and low-modulus medical titanium alloy implant.

BACKGROUND ART

Compared with the medical metal materials such as stainless steel, Co—Cr alloys and the like, titanium alloys, which have excellent biomechanical properties and good biocompatibility, are widely used as the replacement materials and repairs for human hard tissues such as bone trauma products, artificial joints and the like. However, it is found in clinical studies that "stress shielding" effect is appeared in traditional titanium alloys (a titanium alloy, α+β titanium alloy) due to the mismatching of elastic modulus. After long-term implantation in the human body, the traditional titanium alloys will cause the functional degradation and body absorption of the original bone tissues, and the plantation failures resulted therefrom. Meanwhile, the titanium alloys are bio-inert materials, and are difficult to form robust chemical bonding with the bones. After long-term implantation in human bodies, the potential problems such as leaching of toxic ions such as Al, V, and the like, caused by metal corrosion, will occur. Therefore, it is a premise and key point to prepare of a new generation of medical titanium alloy material with good mechanical compatibility and bioactivity in order to ensure the long-term stability and achieve the satisfactory therapeutic effects.

Due to low elastic modulus and high strength, and containing none of toxic elements such as Al, V, and the like, β-type titanium alloys have been widely studied, which mainly comprise Ti—Mo-based, Ti—Nb-based, Ti—Zr-based, Ti—Ta-based alloys, etc., and the typical representative examples comprise Ti-15Mo, Ti-13Nb-13Zr, Ti-12Mo-6Zr-2Fe, Ti-35Nb-5Ta-7Zr, and Ti-29Nb-13Ta-4.6Zr, wherein Ti—Nb—Ta—Zr alloys have low elastic modulus (48-55 GPa) (Materials 2014, 7, 709-1800), which is about 50% of that of Ti-6Al-Vi. However, the current Ti—Nb—Ta—Zr-based titanium alloys are generally low in intensity (~550 GPa) (Materials Science and Engineering C 60 (2016) 230-238), and can not match with the elasticity modulus of human bone tissue (10-30 GPa) (Adv. Eng. Mater. 2019, 1801215), and are hard to form robust chemical bonding with the bones due to the absence of biologically active elements. Therefore, there is a need to prepare a medical titanium alloy with high-strength and low-modulus, and good biocompatibility.

As an emerging technology developing rapidly in the field of manufacture, additive manufacture (also referred to as "3D printing") is directly forming by the principle of layer-by-layer stacking, and has significant advantages such as Near Net Shape Forming of complex parts, personalized customization, and the like. Especially, by means of the characteristics of rapid cooling rate ($10^4$-$10^5$ K/s or more) of Selective Laser Melting (SLM) and Selective Electron Beam Melting (SEBM) in the 3D printing technology (International Materials Reviews 2016 VOL 61 NO 5 361), the fine grain microstructure or even the ultrafine grain microstructure can be obtained in various alloy systems, thereby improving mechanical properties and biocompatibility (RSC Adv., 2015, 5, 101794). Ti-30Nb-5Ta-3Zr alloy prepared by SLM, Luo et al. (Materials Science & Engineering C 97 (2019) 275-284) has the average grain size of 17.6 μm, the tensile strength of 680 MPa, the plasticity of 15.3%, the elastic modulus of 64.2 GPa, but some of the grains have abnormal large size, for example, the grain size of 100-260 μm. The reason that the Ti-30Nb-5Ta-3Zr alloys prepared by the technology SLM are relatively large in the grain size and relatively low in tensile strength is that the SLM has relatively low overlapping rate (~35%), relatively low scanning speed (200-600 mm/s), and the martensite phase change during the forming process rendering the elastic modulus higher than that in the single phase β-Ti alloy. In addition, the studies show that the faster the scanning speed is, the higher the degree of under cooling is, and the less the grain size is (ActaMaterialia 60 (2012) 3849-3860). However, the high cooling speed will cause high thermal stress, resulting in cracking. Furthermore, the high scanning speed will result in the high instability in the molten pool (Journal of Materials Processing Technology 210 (2010) 1624-1631), rendering the formation of holes and reducing the density (ActaMaterialia 108 (2016) 36-45). Therefore, how to solve the contradiction between increasing the scanning speed for refining the grains and increasing the cracking and holes has been a common technical difficulty faced with the current additive manufacturing.

Si, a bioactive element, can not only promote osteoproliferation, cell adhesion, and the formation of robust chemical bonding with bone (RSC Adv., 2015, 5, 101794), but also refine the grains and form the second phase, thereby strengthening the fine grains and the second phase. However, the non-metallic element Si tends to form the continuous grain boundary weakening phase with Ti, thereby severely reducing mechanical properties. In addition, under a high temperature gradient, since the thermal expansion coefficient of the β-Ti matrix is different from that of the Si-containing intermetallic compound, the formation of cracking is accelerated, and thereby increasing the difficulty of 3D printing. Therefore, how to solve the problem of deterioration of mechanical property and molding property caused by the introduction of the bioactive essential element Si is a technical difficulty to be solved at present.

SUMMARY

A primary object of the present invention is to provide an additive manufacturing method of a Si-containing high-strength and low-modulus medical titanium alloy which effectively solves the problem of deterioration of mechanical property and formability caused by the introduction of the bioactive essential element Si.

Another object of the present invention is to provide a Si-containing high-strength and low-modulus medical titanium alloy prepared by the above method.

Still another object of the present invention is to provide the use of the abovementioned Si-containing high-strength and low-modulus medical titanium alloy in the preparation of human body implants.

The objects of the present invention are achieved by the following technical solutions:

An additive manufacturing method of a Si-containing high-strength and low-modulus medical titanium alloy, characterized by comprising the following steps:

(1) Alloy Ingredient Design: 0.1-5 at. % bioactive element Si is added into a low elastic modulus TiNbTaZr-based alloy, then according to the d-electron theory, the average number of bonding times of the alloy $\overline{Bo}$ is calculated by $$\overline{Bo} = \sum_i X_i \cdot (Bo)_i,$$

wherein $(Bo)_i$ is the covalent bond energy determined by the d electronic cloud overlapping between the alloy element i and the matrix alloy element; the average d electron orbital energy level of the alloy $\overline{Md}$ is calculated by $$\overline{Md} = \sum_i X_i \cdot (Md)_i,$$

wherein $(Md)_i$ is the average value of the M–d energy level of the alloy element i, i is the alloy element Nb and Ta, Xi is the atomic percentage of the alloy element i; according to the β-Ti region of the $\overline{Bo}$–$\overline{Md}$ relationship graph, the calculated values of $\overline{Bo}$ and $\overline{Md}$ are selected to fall in the meta-stable-Ti region of the $\overline{Bo}$–$\overline{Md}$ relationship graph, then according to the Ti—Zr—Si ternary phase graph, the alloy ingredient range which is deviated from the eutectic point and close to the maximum solid solubility of Si in Ti is selected, so that the Si-containing high-strength and low-modulus medical titanium alloy is designed to have the alloy ingredients in the ingredient proportion of Ti 60-70 at. %, Nb 16-24 at. %, Zr 4-14 at. %, Ta 1-8 at. %, Si 0.1-5 at. %, by using sponge titanium, sponge zirconium, tantalum niobium intermediate alloy, and elemental silicon, as raw materials.

(2) Powder Preparation: the elements Ti, Nb, Zr, Ta and Si are compounded according to the contents of step (1), melted by a Vacuum Arc Remelting furnace so as to prepare the alloy rods; the titanium alloy powders are prepared by Electrode Induction Melting Gas Atomization method (EIGA) or Plasma Rotating Electrode Processing method (PREP), and sieved so as to obtain the spherical powders having the range of particle sizes suitable for additive manufacturing.

(3) Model construction and substrate preheating: the three-dimensional model of the structural parts to be prepared is constructed, the slicing is completed and the print files are created, the preheating temperature of the substrate in the Selective Laser Melting is 150-650° C., and the preheating temperature of the substrate in the Selective Electron Beam Melting is 650-1200° C. 15

(4) Additive manufacturing molding: the additive manufacturing molding is carried out by a Selective Laser Melting apparatus or a Selective Electron Beam Melting apparatus so as to obtain a high-strength and low-modulus medical titanium alloy; wherein the key molding parameters are: 50%≤the melting channel overlapping rate μ≤80%, 1000 mm/s≤the scanning speed V≤10000 mm/s; in the case of the Selective Laser Melting, the laser input power P, 140 W≤P≤360 W, the laser scanning pitch h of 20-80 μm, and in the case of the Selective Electron Beam Melting, the electron gun current I, 8 mA≤I≤100 mA, and the electron beam scanning pitch h of 20-200 μm.

For further achieving the objects of the present invention, preferably, in step (1), $\overline{Bo}$=2.86~2.90, $\overline{Md}$=2.45~2.47.

Preferably, the Vacuum Arc Remelting process in step (2) comprises: the formulated raw materials are pressed into an electrode, and the size of the electrode is controlled to be 50-70 mm less than that of the crucible; the gap between the electrode and the molten pool is controlled at 60-80 mm, the melting speed is 20 kg/min; the casting ingot is obtained after remelting twice, without significant ingredient precipitation.

Preferably, Electrode Induction Melting Gas Atomization process in step (2) comprises: the melted casting ingot is machined into the bar of ϕ 45 mm×550 mm, without significant oxidation on the surface, one end of the bar is machined into 45° cone, the atomization pressure is 3.5-4.5 MPa, the melting power is 20-30 KW, the feeding speed is 35-45 mm/min, and the whole environment is under inert gas atmosphere.

Preferably, the Plasma Rotating Electrode Processing process in step (2) comprises: the melted ingot is machined into the bar of ϕ 60 mm×650 mm, without significant oxidation on the surface, the atomization power is 50-60 KW, the rotation speed is 16000-18000 r/min, and the whole environment is under inert gas atmosphere.

Preferably, the overlapping rate in step (4) is calculated by $$\mu = \frac{w-h}{w} \times 100\%,$$

wherein w is the width of the molten panel (μm); h is the scanning pitch (μm).

Preferably, in step (4), the powder size suitable for the Selective Laser Melting is 15-53 μm; the powder size suitable for Selective Electron Beam Melting is 45-100 μm.

The selective laser melting apparatus or the selective electron beam melting apparatus for additive manufacturing molding in the present invention comprises EOS M290, SLMsolution 280, RENISHAW 400, Arcam Q10plus, etc.

A Si-containing high-strength and low-modulus medical titanium alloy prepared by the abovementioned method, characterized in that the microstructure of the alloy is consisted of columnar grains of β-Ti and equiaxed grains of β-Ti as matrix, the intragranular uniformly distributed spherical $(Ti, Zr)_2Si$ phase and the grain boundary discontinuously distributed $(Ti, Zr)_2Si$ phase as enforcing phase, wherein the particle size of the β-Ti grains is 1-13 μm, and the size of the spherical $(Ti, Zr)_2Si$ phase grains is 50-300 nm; the grain boundary discontinuously distributed $(Ti, Zr)_2Si$ phase is in strip shape, with the width of 30-200 nm, and the aspect ratio of 1-6.

The use of the Si-containing high-strength and low-modulus medical titanium alloy in the preparation of human body implants.

Preferably, the human body implant comprises femoral head implant, hip joint implant, knee joint implant; vertebral body fusion cage, intervertebral fusion cage; spinal implant, shoulder implant, mandible implant, cranial implant, craniomaxillofacial implant, foot ankle joint implant, toe bone implant or sternal implant.

The principle of the preparation method of the present invention is as follows: by means of the Alloy Ingredient Design in step (1), the element Si having both bioactivity and grain refining effect is introduced in a low elastic modulus TiNbTaZr-based alloy, (as for the Si-free TiNbTaZr alloy, a high degree of undercooling under high-speed scanning is used to refine the grains, and the high overlapping rate is used to ensure the density of the sample), and then $\overline{Bo}$ and $\overline{Md}$ are calculated by $$\overline{Bo} = \sum_i X_i \cdot (Bo)_i \text{ and } \overline{Md} = \sum_i X_i \cdot (Md)_i$$

respectively, and the $\overline{Bo}$ and $\overline{Md}$ are selected to satisfy the meta-stable β-Ti region in the $\overline{Bo}$–$\overline{Md}$ relationship graph (the meta-stable β-Ti has a low elastic modulus) (Materials Science and Engineering A243 (1998) 244-249). However, as for the alloy containing the brittle eutectic compound prepared by the conventional process (such as casting), the cracking problem caused by high cooling speed has not been considered. Therefore, as for the additive manufacturing process with the characteristics of rapid heating and rapid cooling, it is also necessary to consider the specific process. When satisfying the $\overline{Bo}$–$\overline{Md}$ relationship graph, the alloy ingredients are further optimized according to the Ti—Zr—Si alloy phase graph to make the alloy ingredients satisfying the transition from the divorced eutectic reaction at the normal scanning speed to the precipitation reaction at high speed scanning, thereby obtaining the discontinuous microstructure of the second phase.

The powders which satisfy the size requirements of the 3D printing powders are prepared by step (2).

In step (3), the thermal stress generated during the printing process is reduced by the pre-heating of the substrate so as to reduce the tendency of cracking, and the pre-heating temperature is selected to ensure that there is a sufficiently high degree of undercooling in the precipitation reaction, and at the same time the thermal stress caused by the difference of the thermal expansion coefficient between the second phase and the matrix phase is reduced to as much as possible so as to avoid cracking.

In step (4), a high degree of undercooling (namely, high cooling rate) under high-speed scanning is used to obtain the fine grain structure, and at the same time, promote the transition of the alloy from the divorced eutectic reaction to the precipitation reaction, suppress the continuous distribution of the $(Ti, Zr)_2Si$ phase along the grain boundary, promote the intragranular precipitation of the $(Ti, Zr)_2Si$ phase, and in turn improve the mechanical property and biocompatibility of the material. Meanwhile, since the high-speed scanning can reduce the width of the molten pool and form the holes, increasing the overlapping rate can improve the density and the molding quality of the printing product. Therefore, the present patent solves the common technology problem that the mechanical properties and the molding properties of the alloy material are deteriorated due to the precipitation of alloy ingredients out of the continuous grain boundary phase in the divorced eutectic reaction which easily occurs in the additive manufacturing by exploring the appropriate ingredient proportion (which satisfies the meta-stable β-Ti region in the $\overline{B_0}$–$\overline{M_d}$ relationship graph, and at the same time considers the additive manufacturing process to promote the precipitation reaction), and using the high speed scanning and the high overlapping rate to promote the introgranular diffusion and precipitation of the $(Ti, Zr)_2Si$ phase and the discontinuous precipitation at the grain boundary (as for the Si-free TiNbTaZr alloy, the high-speed scanning can also be used to achieve the effects of refining grains and increasing intensity).

Compared with the prior art, the present invention has the following advantages and beneficial effects:

1. Compared with the traditional α-type and α+β-type medical titanium alloys, the medical β-type titanium alloy prepared in the present invention has lower elastic modulus and better biocompatibility, and at the same time, due to the introduction of the second phase, the alloy of the present invention has higher strength (the yield strength of 810 MPa, the tensile strength of 1120 MPa), and lower elastic modulus (~59 GPa). Compared with Ti-6Al-4V ELI (ASTM F136), the alloy of the present invention is slightly increased in the yield strength, and increased in the tensile strength by 260 MPa. Compared with medical β-type titanium alloy Ti-13Nb-13Zr (ASTM F1713), the alloy of the present invention is increased in the yield strength by 85 MPa, increased in the tensile strength by 260 MPa, and decreased in the elastic modulus by 20 GPa; therefore, has significantly better mechanical compatibility and biocompatibility than those in the traditional medical titanium alloys.
2. The present invention provides a guiding idea for the alloy ingredient design and the additive manufacturing of the alloy which easily occurs the divorced eutectic reaction to form continuous distribution of the second phase along the grain boundary.
3. Compared with the traditional casting alloy, the high-strength and low-modulus medical titanium alloy formed by using the additive manufacturing technology of the present invention, due to the characteristics of rapid heating and rapid cooling in SLM/SEBM, has the microstructure comprising finer grains, less ingredient precipitation, therefore has better mechanical properties and biocompatibility.
4. Compared with the traditional casting and plastic deformation, the present invention uses additive manufacturing molding to prepare various parts having complex shape, which satisfies the personalized design requirements, and actually provides the patient the customized medical implants.
5. The SLM/SEBM molding technology used in the present invention can achieve near net shape forming, and improve the utilization rate of materials, thereby saving costs.

BRIEF DESCRIPTION OF THE DRAWINGS

FIG. 1 is the $\overline{Bo}$–$\overline{Md}$ relationship graph in Example 1 (Scripta Materialia 158 (2019) 62-65).

DETAILED DESCRIPTION OF THE INVENTION

For better understanding of the present invention, the present invention will be further described below with reference to examples and drawings, but the embodiments of the present invention are not limited thereto.

The test methods of the following examples are as follows: the sample density is measured by Archimedes method; the tensile properties, such as the yield strength, the tensile strength and the strain at break of the sample are tested according to the international standard (Chinese GB/T 228-2002), the elastic modulus is tested according to the American Standard (ASTM E1876-15); and the biocompatibility is evaluated according to the international standard (GB/T 16886.5-2003).

Example 1

An additive manufacturing method of a Si-containing high-strength and low-modulus medical titanium alloy, comprising the following steps:

(1) Alloy Ingredient Design: the alloy ingredients are formulated in the ingredient proportion of Ti 68.3 at. %, Nb 23.3 at. %, Zr 4.7 at. %, Ta 1.7 at. %, and Si 2 at. %, wherein Bo=2.88, Md=2.46, which satisfy the meta-stable β-Ti region in the $\overline{Bo}$–$\overline{Md}$ relationship graph (the arrow position in FIG. 1, determined by Bo=2.88, Md=2.46), the atomic percentage content of the alloy can be determined by $$\overline{Bo} = \sum_i X_i \cdot (Bo)_i \text{ and } \overline{Md} = \sum_i X_i \cdot (Md)_i,$$

by using sponge titanium, sponge zirconium, tantalum niobium intermediate alloy (solid solution of niobium and tantalum), and elemental silicon as raw materials. FIG. 1 shows $\overline{Bo}$–$\overline{Md}$ relationship graph (Scripta Materialia 158 (2019) 62-65), wherein the shaded portion is the meta-stable β-Ti region.

TABLE 1

Bo and Md values for different alloy elements in bcc-Ti

| electron orbital | element | Bo | Md/eV |
|---|---|---|---|
| 3d | Ti | 2.790 | 2.447 |
|  | Zr | 3.086 | 2.934 |
| 4d | Nb | 3.099 | 2.424 |
| 5d | Ta | 3.144 | 2.531 |
|  | Si | 2.561 | 2.200 |

Table 1 shows the Bo and Md values of each alloy element in bcc-Ti, which belong to the inherent properties of the alloy element itself and are obtained by calculation. The average number of bonding times $\overline{Bo}$ and the average d-orbital energy level $\overline{Md}$ of the alloy can be calculated from each alloy element, wherein the average number of bonding times of the alloy is calculated by $$\overline{Bo} = \sum_i X_i \cdot (Bo)_i$$

(i is the alloy element, for example, Nb and Ta, $X_i$ is the atomic percentage of the alloy element i, $(Bo)_i$ is the covalent bond energy determined by the d-electronic cloud overlapping between the alloy element i and the matrix alloy element), and the average d-electron orbital energy level of the alloy is calculated by $$\overline{Md} = \sum_i X_i \cdot (Md)_i$$

(i is the alloy element, for example, Nb and Ta, $X_i$ is the atomic percentage of the alloy element i, and (Md) is the average value of the M–d energy level of the alloy element i). The $\overline{Bo}$–$\overline{Md}$ relationship graph shows the ranges of $\overline{Bo}$ and $\overline{Md}$ of various titanium alloy types (α, α+β, β+α", β), which can be used as references for designing the meta-stable β-type titanium alloy ingredients. The specific design method is as follows: according to the Ti—Zr—Si phase graph, the content which is away from the eutectic point of the ingredient and close to the maximum solid solubility of Si in Ti is selected, the atomic percentage of Si is 2%, then the contents of other alloy elements are determined from Bo=2.88, Md-2.46, wherein the ingredients of Example 1 are shown at the arrow position.

(2) Powder preparation: the elements Ti, Nb, Zr, Ta and Si are compounded according to the contents in step (1), melted by a Vacuum Arc Remelting furnace at melting speed of 20 kg/min, remelted twice so as to obtain the casting ingots without significant ingredient precipitation. The metal ingots are machined into the round bars of ϕ 45 mm×550 mm, and the surface oxide skins are removed. The alloy powders are prepared by Electrode Induction Melting Gas Atomization method (EIGA) under inert gas atmosphere, at the atomization pressure of 4.0 MPa, the melting power of 25 KW, and the feeding rate of 40 mm/min. Then the resulting powders are subjected to airflow classification and screening treatment, so as to obtain the powders having particle size in the range of 15-53 μm.

(3) Model construction and substrate preheating: the cuboid structure of 50×10×10 is constructed. The constructed cuboid structure is inputted into Magics 15.01 for setting the position and the printing directions. Then, the processed data are imported into the EOSRP-tools software to perform slicing and generate the print files. Then, the substrate is leveled, and the titanium alloy powders with a thickness in the range of 50-100 μm are previously uniformly laid on the Ti-6Al-4V substrate by a powder laying device. The molding chamber is vacuumized to less than 0.6 mbar by a vacuum pump, and Ar gas is charged into the molding chamber, until the oxygen content in the forming chamber is reduced to 0.1% or less. The preheating temperature of the substrate is 180° C. The preheating temperature is selected to ensure that there is a sufficiently high degree of undercooling in the precipitation reaction, at the same time the thermal stress caused by the difference of thermal expansion coefficient between the second phase and the matrix phase is reduced as much as possible, so as to avoid cracking.

(4) Additive manufacturing molding: the additive manufacturing molding is carried out by a selective laser melting apparatus, under the selective laser melting parameters of the overlapping rate of 50%, the laser scanning speed of 2200 mm/s, the laser power, P, of 250 W, the scanning pitch of 50 μm, the powder thickness of 30 μm, and the laser scanning strategy of 67°. The addition of the non-metallic element Si is beneficial to improve biocompatibility, but very easy to form the brittle phase continuously distributed along the grain boundary. The high cooling rate under high speed scanning is used to promote the transition of the alloy ingredients from the divorced eutectic reaction to the precipitation reaction, and in turn, suppress the formation of the brittle phase continuously distributed along the grain boundary and the generation of cracking, promote the intragranular diffusion and precipitation of the second phase, and at the same time, the high overlapping rate is used to compensate the defect of easy formation of holes due to high-speed scanning, thus preparing the titanium alloy sample having fine grain structure or even ultrafine grain structure.

In this example, the titanium alloy formed in step (4) has a density of up to 99.5%, which is nearly full density. The microstructure of the alloy is consisted of columnar grains of β-Ti and equiaxed grains of β-Ti and (Ti, Zr)$_2$Si phase, wherein the columnar grains of β-Ti are epitaxially grown along the boundary of the molten pool, with the grain size of about 3-12 μm; and the equiaxed grains of β-Ti are mainly distributed at the periphery of the molten pool and at the boundary of the molten pool, with the grain size of 1-3 µm. The (Ti, Zr)$_2$Si phase is mainly distributed in the intragranular form and the grain boundary form, wherein the intragranular (Ti, Zr)$_2$Si phase is mainly spherical, with the size of 50-200 nm; and the grain boundary (Ti, Zr)$_2$Si phase is mainly in the interrupted strip shape, with the width of 30-150 nm, and the aspect ratio of 1-4.

Although the addition of the bioactive element Si can achieve the purpose of refining grains and improving biocompatibility, the intermetallic compound (Ti, Zr)$_2$Si phase is readily continuously precipitated at the grain boundary, thus weakening the mechanical properties. The high speed scanning and the high overlapping rate are used to, on one hand, refine the grains, reduce the formation of holes and in turn improve the mechanical properties, and on the other hand, suppress the divorced eutectic reaction and promote the precipitation reaction, and in turn suppress the continuous precipitation of (Ti, Zr)$_2$Si at the grain boundary, thus achieving the effects of strengthening the solid solution and strengthening the second phase. Therefore, the medical titanium alloy excellent in mechanical compatibility and biocompatibility can be obtained only when the combination of high speed scanning and high overlapping rate is used.

The titanium alloy parts manufactured by using the high speed scanning method described in this example have the yield strength of up to 810 MPa, the tensile strength of 1120 MPa, the strain at break of 6.4%, and the elastic modulus of ~59 GPa. Compared with Ti-6Al-4V ELI (ASTM F136), the alloy of this example is slightly increased in the yield strength, increased in the tensile strength by 260 MPa, and decreased in the elastic modulus by 51 GPa. Compared with the medical β-type titanium alloy Ti-13Nb-13Zr (ASTM F1713), the alloy of this example is increased in the yield strength by 85 MPa, increased in the tensile strength by 260 MPa, and decreased in the elastic modulus by 20 GPa. Obviously, compared with the medical titanium alloy implant of the current clinical application, the alloy in example 1 has higher strength and lower elastic modulus, which can effectively reduce the "stress shielding" effect caused by the mismatching of the elastic modulus, and avoid the functional degradation and the body absorption of the original bone tissue caused by long-term implantation of human body, and the implanting failure resulted therefrom. In addition, the cell proliferation experiment of Example 1 shows that the absorbance (OD value) detected by the microplate reader at 1 day, 4 days and 7 days is 0.07, 0.8, 2.1, respectively, which is significantly superior to those in Ti-6Al-4V ELI (0.04, 0.6 and 1.6). Meanwhile, the cytotoxicity experiments of Example 1 shows that the cell surviving number after 24 h (live cell staining area per unit area) is 15.3%, which is also higher than that of Ti-6Al-4V ELI (11.3%). Compared with Ti-6Al-4V ELI, the alloy of Example 1, which contains the bioactive element Si and does not contain the toxic elements such as Al and V, greatly promotes the cell proliferation and exhibits lower biotoxicity, therefore, has better mechanical compatibility and biocompatibility than those in the traditional medical titanium alloys.

Example 2

An additive manufacturing method of a Si-containing high-strength and low-modulus medical titanium alloy, comprising the following steps:
(1) Alloy Ingredient Design: the alloy ingredients formulated in the ingredient proportion of Ti 68.3 at. %, Nb 23.3 at. %, Zr 4.7 at. %, Ta 1.7 at. %, and Si 2 at. %, wherein Bo=2.88, Md=2.46, which satisfy the metastable β-Ti region in the $\overline{Bo}$–$\overline{Md}$ relationship graph, by using sponge titanium, sponge zirconium, tantalum niobium intermediate alloy, and elemental silicon as raw materials.
(2) Powder preparation: the elements Ti, Nb, Zr, Ta and Si are compounded according to the contents in step (1), melted by a Vacuum Arc Remelting furnace at melting speed of 20 kg/min, remelted twice so as to obtain the casting ingots without significant ingredient precipitation. The metal ingots are machined into the round bars of φ 60 mm×650 mm, and the surface oxide skins are removed. The alloy powders are prepared by Plasma Rotating Electrode Processing method (PREP) under inert gas atmosphere, with the atomization power of 55 KW, the rotation speed of 17000 r/min. Then the resulting powders are subjected to airflow classification and screening treatment, so as to obtain the powders having particle size in the range of 45-100 µm.
(3) Model construction and substrate preheating: the cuboid structure of 50×10×10 is constructed. The constructed cuboid structure is input into Magics 15.01 for setting the position and the printing direction, then the processed data are imported into BuildAssembler software to perform slicing and generate the print files. The substrate is leveled, and the amount of powders in the powder boxes on both sides is adjusted. Then the molding chamber is vacuumized to less than 5×10$^{-3}$ Pa by a vacuum pump. The substrate is preheated to 650° C. The preheating temperature of the substrate is 180° C. The preheating temperature is selected to ensure that there is a sufficiently high degree of undercooling in the precipitation reaction, and the same time the thermal stress caused by the difference of the thermal expansion coefficient between the second phase and the matrix phase is reduced as much as possible so as to avoid cracking.
(4) 3D printing molding: 3D printing molding is carried out by an selective electron beam melting apparatus, with the selective electron beam melting parameters of: the overlapping rate of 80%, the electron beam scanning speed of 4530 mm/s, the current I of 38 mA, the scanning pitch of 20 µm, the scanning strategy of 90°, and powder thickness of 50 µm. The addition of the non-metallic element Si is beneficial to improve biocompatibility, but easy to form the brittle phase continuously distributed along the grain boundary. The high cooling rate under high speed scanning is used to promote the transition of the alloy ingredients from the divorced eutectic reaction to the precipitation reaction, and in turn, suppress the formation of the brittle phase continuously distributed along the grain boundary and the generation of cracking, promote the intragranular diffusion and precipitation of the second phase, and at the same time, the high overlap rate is used to compensate the defect of easy formation of holes due to high-speed scanning, thereby preparing the titanium alloy sample having fine grain structure or even ultrafine grain structure.

In this example, the titanium alloy formed under the above ranges of processing parameters has a density of up to 99.7%, which is a nearly full density. The phase composition of the titanium alloy comprises β-Ti as a matrix, with the grain size of 1-9 µm, which size is less than that in Example 1; the (Ti, Zr)$_2$Si phase mainly precipitated in intragranular form and grain boundary form, wherein the intragranular (Ti, Zr)$_2$Si phase is spherical, with the size of 50-150 nm; the grain boundary (Ti, Zr)$_2$Si phase is interruptedly distributed along the grain boundary, with the width of 30-100 nm, and the aspect ratio of 1-3. The titanium alloy in this example has the tensile strength of 1090 MPa, the yield strength of 790 MPa, the elastic modulus of ~57 GPa. Compared with Ti-6Al-4V ELI (ASTM F136), the medical titanium alloy prepared in this example is slightly increased in the yield strength, increased in the tensile strength by 230 MPa, and decreased in the elastic modulus by 53 GPa. Compared with the medical β-type titanium alloy Ti-13Nb-13Zr (ASTM F1713), the alloy in this example is increased in the yield strength by 65 MPa, increased in the tensile strength by 230 MPa, and decreased in the elastic modulus by 22 GPa. In addition, the cell proliferation experiment of Example 2 shows that the absorbance (OD values) detected by the microplate reader at 1 day, 4 days and 7 days is 0.07, 0.8, 2.0, respectively, which is significantly superior to those in Ti-6Al-4V ELI (0.04, 0.6 and 1.6). Meanwhile, the cytotoxicity experiment of Example 2 shows that the cell surviving number after 24 h (live cell staining area per unit area) is 15.1%, which is also higher than that in Ti-6Al-4V ELI (11.3%). Obviously, compared with the medical titanium alloy implant of the current clinical application, the alloy of Example 2 has higher strength and lower elastic modulus, which can effectively reduce the "stress shielding" effect caused by the mismatching of the elastic modulus, avoid the functional degradation and body absorption of the original bone tissue caused by long-term implantation of the human body, and the implanting failure resulted therefrom, and at the same time, has significantly better biocompatibility than that of the traditional medical titanium alloy.

Example 3

An additive manufacturing method of a Si-containing high-strength and low-modulus medical titanium alloy, comprising the following steps:
  (1) Alloy Ingredient Design: the alloy ingredients are formulated in the ingredient proportion of Ti 69.6 at. %, Nb 23.7 at. %, Zr 4.8 at. %, Ta 1.7 at. %, Si 0.1 at. %, wherein $\overline{Bo}$=2.88, $\overline{Md}$=2.47, which satisfy the metastable β-Ti region in the $\overline{Bo}$–$\overline{Md}$ relationship graph, by using sponge titanium, sponge zirconium, tantalum niobium intermediate alloy as raw materials.
  (2) Powder preparation: the elements Ti, Nb, Zr, Ta and Si are compounded according to the contents in step (1), melted by a vacuum arc remelting furnace at melting speed of 20 kg/min, remelted twice so as to obtain the casting ingots without significant ingredient precipitation. The metal ingots are machined into the round bars of φ 45 mm×550 mm, and the surface oxide shins are removed. The alloy powders are prepared by Electrode Induction Melting Gas Atomization (EIGA) under inert gas atmosphere, with the atomization pressure of 4.0 MPa, the melting power of 25 KW, and the feeding rate of 40 mm/min. Then the resulting powders are subjected to airflow classification and screening treatment, so as to obtain the powders having particle size in the range of 15-53 μm.
  (3) Model construction and substrate preheating: the cuboid structure of 50×10×10 is contructed. The constructed cuboid structure is inputted into Magics 15.01 for setting the position and the printing direction. Then, the processed data are imported into the EOSRPtools software to perform slicing and generate the print files. Then, the substrate is leveled, and the titanium alloy powders with a thickness in the range of 50-100 μm are previously uniformly laid on the Ti-6Al-4V substrate by a powder laying device. The molding chamber is vacuumized to less than 0.6 mbar by a vacuum pump, and Ar gas is charged into the molding chamber, until the oxygen content in the molding chamber is reduced to 0.1% or less; The preheating temperature of the substrate is 180° C. The preheating temperature is selected to ensure that there is a sufficiently high degree of undercooling in the precipitation reaction, and at the same time the thermal stress caused by the difference of the thermal expansion coefficient between the second phase and the matrix phase is reduced as much as possible, so as to avoid cracking.
  (4) Additive manufacturing molding: additive manufacturing molding is carried out by a selective laser melting apparatus, under the selective laser melting parameters of: the overlapping rate of 70%, the laser scanning speed of 3000 mm/s, the laser power, P, of 360 W, the scanning pitch of 40 μm, the powder thickness of 40 μm, and the laser scanning strategy of 67°. In the Example 3, although no Si element is added, the high overlapping rate and high scanning speed can be used to achieve the effects of refining grains as well, thereby improving the mechanical properties and biocompatibility of the alloy.

In this example, the titanium alloy formed in the above range of processing parameters has a density of up to 99.7%, which is nearly full density. The phase composition of the titanium alloy comprises the columnar grains of β-Ti as a matrix, with the grain size of 2-13 μm, the tensile strength of 932 MPa, the yield strength of 896 MPa, and the plasticity at break of 19%. Compared with the Ti-30Nb-5Ta-3Zr alloy prepared by SLM in Reference 1, since the grains are finer under high speed scanning, the medical titanium alloy prepared in this example is increased in the tensile strength by 252 MPa, increased in the yield strength by 232 MPa, increased in the plasticity by 3.7%, and decreased in the elastic modulus by 12 GPa. Compared with Ti-6Al-4V ELI (ASTM F136), the alloy in this example is reduced in the elastic modulus by 58 GPa. In addition, the cell proliferation experiment of Example 3 shows that the absorbance (OD value) detected by the microplate reader at 1 day, 4 days and 7 days is 0.06, 0.7, 1.8, respectively, which is slightly superior over that in Ti-6Al-4V ELI (0.04, 0.6 and 1.6). Meanwhile, the cytotoxicity experiment of Example 3 shows that the cell surviving number after 24 h (live cell staining area per unit area) is 13.7%, which is also higher than that in Ti-6Al-4V ELI (11.3%). Obviously, compared with the medical titanium alloy implant of the current clinical application, the alloy of Example 3 has smaller grains, higher strength and lower elastic modulus, which can effectively reduce the "stress shielding" effect caused by the mismatching of elastic modulus, and avoid the functional degradation and body absorption of the original bone tissue caused by long-term implantation of the human body, and the implantation failure resulted therefrom, and at the same time due to the absence of biotoxic elements such as Al and V, exhibits relatively good biocompatibility.

Example 4

An additive manufacturing method of a Si-containing high-strength and low-modulus medical titanium alloy, comprising the following steps:
  (1) Alloy Ingredient Design: the alloy ingredients are formulated in the ingredient proportion of Ti 67 at. %, Nb 21.8 at. %, Zr 6 at. %, Ta 4.2 at. %, and Si 1 at. %, wherein $\overline{Bo}$=2.86, $\overline{Md}$=2.45, which satisfy the metastable β-Ti region in the $\overline{Bo}$–$\overline{Md}$ relationship graph, by using sponge titanium, sponge zirconium, tantalum niobium intermediate alloy, and elemental silicon as raw materials.

(2) Powder preparation: the elements Ti, Nb, Zr, Ta and Si are compounded according to the contents in step (1), melted by a Vacuum Arc Remelting furnace at melting speed of 20 kg/min, remelted twice so as to obtain the casting ingots without significant ingredient precipitation. The metal ingots are machined into the round bars of ϕ 60 mm×650 mm, and the surface oxide skins are removed. The alloy powders are prepared by Plasma Rotating Electrode Processing method (PREP) under inert gas atmosphere, at the atomization power of 55 KW, the rotation speed of 17000 r/min. Then the resulting powders are subjected to airflow classification and screening treatment, so as to obtain the powders having particle size in the range of 45~100 μm.

(3) Model construction and substrate preheating: the cuboid structure of 50×10×10 is constructed. The constructed cuboid structure is input into Magics 15.01 for setting the position and the printing direction, then the processed data are imported into BuildAssembler software to perform slicing and generate print files. Then the substrate is leveled, and the amount of powders in the powder boxes on both sides is adjusted. Then the molding chamber is vacuumized to less than $5 \times 10^{-3}$ Pa by a vacuum pump, and the substrate is pre-heated to 650° C. The preheating temperature is selected to ensure that there is a sufficiently high degree of undercooling in the precipitation reaction, and at the same time, the thermal stress caused by the difference in the thermal expansion coefficient between the second phase and the matrix phase is reduced as much as possible, so as to avoid cracking.

(4) 3D printing molding: 3D printing molding is carried out by an Selective electron beam melting apparatus, under the selective electron beam melting parameters of: the overlapping rate of 50%, the electron beam scanning speed of 8000 mm/s, the current I of 56 mA, the scanning pitch of 60 μm, the scanning strategy of 90°, and the powder thickness of 50 μm. The addition of the non-metallic element Si is beneficial to improve biocompatibility, but very easy to form the brittle phase continuously distributed along the grain boundary. The high cooling rate under high speed scanning is used to promote the transition of the alloy ingredients from the divorced eutectic reaction to the precipitation reaction, and in turn, suppress the formation of the brittle phase continuously distributed along the grain boundary and the generation of cracking, promote the intragranular diffusion and precipitation of the second phase, and at the same time, the high overlapping rate is used compensate the defect of easy formation of holes due to high-speed scanning, thereby preparing the titanium alloy sample having fine grain structure or even ultra-fine grain structure.

In this example, the titanium alloy formed under the above range of processing parameters has a density of up to 99.7%, which is nearly full density. The phase composition of the alloy comprises β-Ti as a matrix, with the grain size of 1-8 μm, which size is less than that in Example 1; the (Ti, Zr)$_2$Si phase mainly precipitated in intragranular form and grain boundary form, wherein the intragranular (Ti, Zr)$_2$Si phase is spherical, with the size of 50-100 nm; and the grain boundary (Ti, Zr)$_2$Si phase is interruptedly distributed along the grain boundary, with the width of 30-100 nm, and the aspect ratio of 1-3. Compared with Ti-6Al-4V ELI (ASTM F136), the medical titanium alloy prepared in this example is comparable in the yield strength, increased in the tensile strength by 190 MPa, and decreased in the elastic modulus by 56 GPa. Compared with the medical β-type titanium alloy Ti-13Nb-13Zr (ASTM F1713), the medical titanium alloy prepared in this example is increased in the yield strength by 50 MPa, increased in the tensile strength by 190 MPa, and decreased in the elastic modulus by 25 GPa. In addition, the cell proliferation experiment of Example 2 shows that the absorbance (OD value) detected by the microplate reader at 1 day, 4 days and 7 days is 0.07, 0.8, 1.9, respectively, which is significantly superior to those of Ti-6Al-4V ELI (i.e., 0.04, 0.6 and 1.6). Meanwhile, the cytotoxicity experiment of Example 4 shows that the cell surviving number after 24 h (live cell staining area per unit area) is 14.2%, which is also higher than that in Ti-6Al-4V ELI (11.3%). Obviously, compared with the medical titanium alloy implant of the current clinical application, the alloy of Example 4 has higher strength and lower elastic modulus, which can effectively reduce the "stress shielding" effect caused by the mismatching of the elastic modulus, and avoid the functional degradation and body absorption of the original bone tissue caused by long-term implantation of the human body and the implanting failure resulted therefrom, and has significantly better mechanically compatibility and biocompatibility than those in the traditional medical titanium alloys.

Example 5

An additive manufacturing method for a Si-containing high-strength and low-modulus medical titanium alloy, comprising the following steps:

(1) Alloy Ingredient Design: the alloy ingredients are formulated in the ingredient proportion of Ti 67.6 at. %, Nb 23 at. %, Zr 4.7 at. %, Ta 1.7 at. %, and Si 3 at. %, wherein $\overline{Bo}$=2.88, $\overline{Md}$=2.46, which satisfy the metastable β-Ti region of the $\overline{Bo}$–$\overline{Md}$ relationship graph, by using sponge titanium, sponge zirconium, tantalum niobium intermediate alloy, and elemental silicon as raw materials.

(2) Powder preparation: the elements Ti, Nb, Zr, Ta and Si are compounded according to the contents of step (1), melted by a Vacuum Arc Remelting furnace at melting speed of 20 kg/min, remelted twice so as to obtain the casting ingots without significant ingredient precipitation. The metal ingots are machined into the round bars of ϕ 45 mm×550 mm, and the surface oxide skins are removed. The alloy powders are prepared by Electrode Induction Melting Gas Atomization method (EIGA) under inert gas atmosphere, at the atomization pressure of 4.0 MPa, the melting power of 25 KW, and the feeding rate of 40 mm/min. And then the resulting powders are subjected to airflow classification and screening treatment, so as to obtain the powders having particle size in the range of 15-53 μm.

(3) Model construction and substrate preheating: the cuboid structure of 50×10×10 is constructed. The constructed cuboid structure is inputted into Magics 15.01 for setting the position and the printing direction. Then, the processed data are imported into the EOSRPtools software to perform slicing and generate the print files. Then, the substrate is leveled, and the titanium alloy powders with a thickness in the range of 50-100 μm are previously uniformly laid on the Ti-6Al-4V substrate by a powder laying device. The molding chamber is vacuumized to less than 0.6 mbar by a vacuum pump, and Ar gas is charged into the molding chamber, until the oxygen content in the molding chamber is reduced to 0.1% or less. The preheating temperature of the substrate is 180° C. The preheating temperature is selected to ensure that there is a sufficiently high degree of undercooling in the precipitation reaction, at the same time, the thermal stress caused by the difference in the thermal expansion coefficient between the second phase and the matrix phase is reduced as much as possible, so as to avoid cracking.

(4) Additive manufacturing molding: additive manufacturing molding is carried out by a Selective Laser Melting apparatus, under the Selective Laser Melting parameters of: the overlapping rate of 60%, the laser scanning speed of 2200 mm/s, the laser power, P, of 250 W, the scanning pitch of 40 μm, the powder thickness of 30 μm, and the laser scanning strategy of 67°. The addition of the non-metallic element Si is beneficial to improve biocompatibility, but very easy to form the brittle phase continuously distributed along the grain boundary. The high cooling rate under high speed scanning is used to promote the transition of the alloy ingredients from the divorced eutectic reaction to the precipitation reaction, and in turn, suppress the formation of the brittle phase continuously distributed along the grain boundary and the generation of cracking, promote the intragranular diffusion and precipitation of the second phase, and at the same time, the high overlapping rate is used to compensate the defect of easy formation of holes due to high-speed scanning, thereby preparing the titanium alloy sample having fine grain structure or even ultrafine grain structure.

In this example, the titanium alloy formed in the above range of processing parameters has a density of up to 99.6%, which is nearly full density. The phase composition of the alloy comprises β-Ti as a matrix, with the grain size of 1-8 μm, which size is less than that in Example 1; the $(Ti, Zr)_2Si$ phase mainly precipitated in the intragranular form and the grain boundary form, wherein the intragranular $(Ti, Zr)_2Si$ phase is spherical, with the size of 50-300 nm; and the grain boundary $(Ti, Zr)_2Si$ phase is interruptedly distributed along the grain boundary, with the width of 50-200 nm, and the aspect ratio of 1-3. Compared with Ti-6Al-4V ELI (ASTM F136), the medical titanium alloy prepared in this example is increased in the yield strength by 30 MPa, increased in the tensile strength by 290 MPa, and decreased in the elastic modulus by 46 GPa. Compared with the medical β-type titanium alloy Ti-13Nb-13Zr (ASTM F1713), the medical titanium alloy prepared in this example is increased in the yield strength by 105 MPa, increased in the tensile strength by 290 MPa, and decreased in the elastic modulus by 15 GPa. In addition, the cell proliferation experiment of Example 2 shows that the absorbance (OD value) detected by the microplate reader at 1 day, 4 days and 7 days is 0.07, 0.9, 2.3, respectively, which is significantly superior to those in Ti-6Al-4V ELI (0.04, 0.6 and 1.6). Meanwhile, the cytotoxicity experiment of Example 5 shows that the cell surviving number after 24 h (live cell staining area per unit area) is 15.6%, which is also higher than that in Ti-6Al-4V ELI (11.3%). Obviously, compared with the medical titanium alloy implant of the current clinical application, the alloy in Example 5 has higher strength and lower elastic modulus, which can effectively reduce the "stress shielding" effect due to the mismatching of the elastic modulus, avoid the functional degradation and body absorption of the original bone tissue caused by long-term implantation of the human body, and the implanting failure resulted therefrom, and has significantly better mechanically compatibility and biocompatibility than those in the traditional medical titanium alloy.

Example 6

An additive manufacturing method for a Si-containing high-strength and low-modulus medical titanium alloy, comprising the following steps:

(1) Alloy Ingredient Design: the alloy ingredients are formulated in the ingredient proportion of Ti 60 at. %, Nb 20.6 at. %, Zr 5 at. %, Ta 9.4 at. %, and Si 5 at. %, where Bo=2.9, Md=2.47, which satisfy the meta-stable β-Ti region of the $\overline{Bo}$–$\overline{Md}$ relationship graph, by using sponge titanium, sponge zirconium, tantalum niobium intermediate alloy, and elemental silicon as raw materials.

(2) Powder preparation: the elements Ti, Nb, Zr, Ta and Si are compounded according to the contents in step (1), melted by a Vacuum Arc Remelting furnace, with the melting speed of 20 kg/min, and remelted twice so as to obtain the casting ingots without significant ingredient precipitation. The metal ingots are machined into the round rods of ϕ 60 mm×650 mm, and the surface oxide skins are removed. The alloy powders are prepared by Plasma Rotating Electrode Processing method (PREP) under inert gas atmosphere, with the atomization power of 55 KW, the rotation speed of 17000 r/min. Then the resulting powders are subjected to airflow classification and screening treatment, so as to obtain the powders having particle size in the range of 45-100 μm.

(3) Model construction and substrate preheating: the cuboid structure of 50×10×10 is constructed. The constructed cuboid structure is input into Magics 15.01 for setting the position and the printing direction, then the processed data are imported into BuildAssembler software to perform slicing and generate the print files. Then the substrate is leveled, and the amount of powders in the powder boxes on both sides is adjusted. Then the molding chamber is vacuumized to below $5×10^{-3}$ Pa by a vacuum pump. The substrate is preheated to 1200° C., wherein the preheating temperature is selected to ensure that there is a sufficiently high degree of undercooling in the precipitation reaction, and at the same time, the thermal stress caused by the difference in the thermal expansion coefficient between the second phase and the matrix phase is reduced as much as possible, so as to avoid cracking.

(4) 3D printing molding: 3D printing molding is carried out by an Selective electron beam melting apparatus, with the Selective electron beam melting parameters of: the overlapping rate of 70%, the electron beam scanning speed of 1000 mm/s, the current I of 64 mA, the scanning pitch of 40 μm, the scanning strategy of 90°, and the powder thickness of 50 μm. The addition of the non-metallic element Si is beneficial to improve biocompatibility, but very easy to form the brittle phase continuously distributed along the grain boundary. The high cooling rate under high speed scanning is used to promote the transition of the alloy ingredients from the divorced eutectic reaction to the precipitation reaction, and in turn, suppress the formation of the brittle phase continuously distributed along the grain boundary and the generation of cracking, promote the intragranular diffusion and precipitation of the second phase, and at the same time, the high overlapping rate is used to compensate the defect of easy formation of holes due to high-speed scanning, thereby preparing the titanium alloy sample having fine grain structure or even ultra-fine grain structure.

In this example, the titanium alloy formed in the above range of processing parameters has a density of up to 99.7%, which is nearly full density. The phase composition of the titanium alloy comprises β-Ti as a matrix, with the grain size of 1-7 μm, which size is less than that in Example 1; the (Ti, Zr)$_2$Si phase mainly precipitated in the intragranular form and the grain boundary form, wherein the intragranular (Ti, Zr)$_2$Si phase is spherical, with the size of 50-200 nm; the grain boundary (Ti, Zr)$_2$Si phase is interruptedly distributed along the grain boundary, with the width of 30-150 nm, and the aspect ratio of 1-6. Compared with Ti-6Al-4V ELI (ASTM F136), the medical titanium alloy prepared in this example is increased in the yield strength by 45 MPa, increased in the tensile strength by 320 MPa, and decreased in the elastic modulus by 41 GPa. Compared with the medical β-type titanium alloy Ti-13Nb-13Zr (ASTM F1713), the medical titanium alloy prepared in this example is increased in the yield strength by 120 MPa, increased in the tensile strength by 320 MPa, and decreased in the elastic modulus by 10 GPa. In addition, the cell proliferation experiment of Example 2 shows that the absorbance (OD value) detected by the microplate reader at 1 day, 4 days and 7 days is 0.07, 0.9, 2.3, respectively, which is significantly superior to those in Ti-6Al-4V ELI (0.04, 0.6 and 1.6). Meanwhile, the cytotoxicity experiment of Example 6 shows that the cells surviving number after 24 h (live cell staining area per unit area) is 16.7%, which is also higher than that in Ti-6Al-4V ELI (11.3%). Obviously, compared with the medical titanium alloy implant of the current clinical application, the alloy in Example 6 has higher strength and lower elastic modulus, which can effectively reduce the "stress shielding" effect caused by the mismatching of the elastic modulus, avoid the functional degradation and body absorption of the original bone tissue caused by long-term implantation of the human body, and implanting failure resulted therefrom, and has significantly better mechanically compatibility and biocompatibility than those in the traditional medical titanium alloy.

It should be noted that the above examples do not constitute limitations on the scope of protection of the present invention, and equivalent replacements or changes are made according to the technical solutions of the present invention and the inventive concepts thereof, which all belong to the scope of protection of the present invention.

The invention claimed is:

1. An additive manufacturing method of a Si-containing high-strength and low-modulus medical titanium alloy, characterized by comprising the following steps:
   (1) Alloy Ingredient Design: 0.1-5 at. % bioactive element Si is added into a low elastic modulus TiNbTaZr-based alloy, then according to the d-electron theory, the average number of bonding times of the alloy $\overline{Bo}$ is calculated by $$\overline{Bo} = \sum_i X_i \cdot (Bo)_i,$$

wherein (Bo)$_i$ is the covalent bond energy determined by the d electronic cloud overlapping between the alloy element i and the matrix alloy element; the average d electron orbital energy level of the alloy $\overline{Md}$ is calculated by $$\overline{Md} = \sum_i X_i \cdot (Md)_i,$$

wherein (Md)$_i$ is the average value of the M–d energy level of the alloy element i, i is the alloy element Nb and Ta, Xi is the atomic percentage of the alloy element i; according to a β-Ti region of a $\overline{Bo}$–$\overline{Md}$ relationship graph, the calculated values of $\overline{Bo}$ and $\overline{Md}$ are selected to fall in a meta-stable β-Ti region of the $\overline{Bo}$–$\overline{Md}$ relationship graph; then according to a Ti—Zr—Si ternary phase graph, the alloy ingredient range which is deviated from the eutectic point and close to the maximum solid solubility of Si in Ti is selected, so that the alloy ingredients of the Si-containing high-strength and low-modulus medical titanium alloy are formulated in the ingredient proportion of Ti 60-70 at. %, Nb 16-24 at. %, Zr 4-14 at. %, Ta 1-8 at. %, Si 0.1-5 at. %, by using sponge titanium, sponge zirconium, tantalum niobium intermediate alloy, and elemental silicon, as raw materials;

(2) Powder Preparation: the elements Ti, Nb, Zr, Ta and Si are compounded according to the contents of step (1), melted by a Vacuum Arc Remelting furnace so as to prepare an alloy rod, the titanium alloy powders are prepared by Electrode Induction Melting Gas Atomization method (EIGA) or Plasma Rotating Electrode Processing method (PREP), and sieved so as to obtain spherical powders having the range of particle sizes suitable for the additive manufacturing;

(3) Model construction and substrate preheating: the three-dimensional model of the structural parts to be prepared is constructed, slicing is completed and print files are created, the preheating temperature of the substrate in Selective Laser Melting is 150-650° C., and the preheating temperature of the substrate in Selective Electron Beam Melting is 650-1200° C.;

(4) Additive manufacturing molding: the additive manufacturing molding is carried out by a Selective Laser Melting apparatus or a Selective Electron Beam Melting apparatus so as to obtain a high-strength and low-modulus medical titanium alloy; wherein the key molding parameters are: 50%≤melting channel overlapping rate μ≤80%, 1000 mm/s≤scanning speed V≤10000 mm/s; in the case of the Selective Laser Melting, the laser input power P is 140 W≤P≤360 W, the laser scanning pitch h is 20-80 μm, and in the case of the Selective Electron Beam Melting, the electron gun current I is 8 mA≤I≤100 mA and the electron beam scanning pitch h is 20-200 μm.

2. The additive manufacturing method for a Si-containing high-strength and low-modulus medical titanium alloy according to claim 1, characterized in that: in step (1), $\overline{Bo}$=2.86~2.90, $\overline{Md}$=2.45~2.47.

3. The additive manufacturing method for a Si-containing high-strength and low-modulus medical titanium alloy according to claim 1, characterized in that: in step (2), the Vacuum Arc Remelting process comprises: the formulated raw materials are pressed into an electrode, wherein the size of the electrode is controlled to be 50-70 mm less than that of a crucible; the gap between the electrode and the molten pool is controlled between 60-80 mm; the melting speed is 20 kg/min; casting ingots are obtained by remelting twice, without significant ingredient precipitation.

4. The additive manufacturing method for a Si-containing high-strength and low-modulus medical titanium alloy according to claim 3, characterized in that: in step (2), the Electrode Induction Melting Gas Atomization method comprises: the casting ingots are machined into the alloy rod of ϕ 45 mm×550 mm, without significant surface oxidation, and one end of the alloy rod is machined into a 45° cone, under inert gas atmosphere, at the atomization pressure of 3.5-4.5 MPa, the melting power of 20-30 KW, and the feeding rate of 35-45 mm/min.

5. The additive manufacturing method for a Si-containing high-strength and low-modulus medical titanium alloy according to claim 3, characterized in that: in step (2), the Plasma Rotating Electrode Processing method comprises: the casting ingots are machined into the alloy rod of ϕ 60 mm×650 mm, without significant surface oxidization, under inert gas atmosphere, at the atomization power of 50-60 KW, and the rotation speed of 16000-18000 r/min.

6. The additive manufacturing method for a Si-containing high-strength and low-modulus medical titanium alloy according to claim 1, characterized in that: in step (4), the overlapping rate is calculated by $$\mu = \frac{w-h}{w} \times 100\%,$$

wherein w is the width of the molten pool (μm); and h is the scanning pitch (μm).

7. The additive manufacturing method for a Si-containing high-strength and low-modulus medical titanium alloy according to claim 1, characterized in that: in step (4), the powder size suitable for the Selective Laser Melting is 15-53 μm; and the powder size suitable for the Selective Electron Beam Melting is 45-100 μm.

8. A Si-containing high-strength and low-modulus medical titanium alloy, characterized in that it is prepared by the method according to claim 1, and the microstructure of the alloy comprises the columnar grains of β-Ti and the equiaxed grains of β-Ti as matrix, the intragranular uniformly distributed spherical $(Ti, Zr)_2Si$ phase and the grain boundary discontinuously distributed $(Ti, Zr)_2Si$ phase as reinforcing phase, wherein the size of the β-Ti grains is 1-13 μm, and the size of the spherical $(Ti, Zr)_2Si$ phase grains is 50-300 nm; and the grain boundary discontinuously distributed $(Ti, Zr)_2Si$ phase is in a strip shape, with the width of 30-200 nm, and the aspect ratio of 1-6.

9. A Si-containing high-strength and low-modulus medical titanium alloy, characterized in that it is prepared by the method according to claim 2, and the microstructure of the alloy comprises the columnar grains of β-Ti and the equiaxed grains of β-Ti as matrix, the intragranular uniformly distributed spherical $(Ti, Zr)_2Si$ phase and the grain boundary discontinuously distributed $(Ti, Zr)_2Si$ phase as reinforcing phase, wherein the size of the β-Ti grains is 1-13 μm, and the size of the spherical $(Ti, Zr)_2Si$ phase grains is 50-300 nm; and the grain boundary discontinuously distributed $(Ti, Zr)_2Si$ phase is in a strip shape, with the width of 30-200 nm, and the aspect ratio of 1-6.

10. A Si-containing high-strength and low-modulus medical titanium alloy, characterized in that it is prepared by the method according to claim 3, and the microstructure of the alloy comprises the columnar grains of β-Ti and the equiaxed grains of β-Ti as matrix, the intragranular uniformly distributed spherical $(Ti, Zr)_2Si$ phase and the grain boundary discontinuously distributed $(Ti, Zr)_2Si$ phase as reinforcing phase, wherein the size of the β-Ti grains is 1-13 μm, and the size of the spherical $(Ti, Zr)_2Si$ phase grains is 50-300 nm; and the grain boundary discontinuously distributed $(Ti, Zr)_2Si$ phase is in a strip shape, with the width of 30-200 nm, and the aspect ratio of 1-6.

11. A Si-containing high-strength and low-modulus medical titanium alloy, characterized in that it is prepared by the method according to claim 4, and the microstructure of the alloy comprises the columnar grains of β-Ti and the equiaxed grains of β-Ti as matrix, the intragranular uniformly distributed spherical $(Ti, Zr)_2Si$ phase and the grain boundary discontinuously distributed $(Ti, Zr)_2Si$ phase as reinforcing phase, wherein the size of the β-Ti grains is 1-13 μm, and the size of the spherical $(Ti, Zr)_2Si$ phase grains is 50-300 nm; and the grain boundary discontinuously distributed $(Ti, Zr)_2Si$ phase is in a strip shape, with the width of 30-200 nm, and the aspect ratio of 1-6.

12. A Si-containing high-strength and low-modulus medical titanium alloy, characterized in that it is prepared by the method according to claim 5, and the microstructure of the alloy comprises the columnar grains of β-Ti and the equiaxed grains of β-Ti as matrix, the intragranular uniformly distributed spherical $(Ti, Zr)_2Si$ phase and the grain boundary discontinuously distributed $(Ti, Zr)_2Si$ phase as reinforcing phase, wherein the size of the β-Ti grains is 1-13 μm, and the size of the spherical $(Ti, Zr)_2Si$ phase grains is 50-300 nm; and the grain boundary discontinuously distributed $(Ti, Zr)_2Si$ phase is in a strip shape, with the width of 30-200 nm, and the aspect ratio of 1-6.

13. A Si-containing high-strength and low-modulus medical titanium alloy, characterized in that it is prepared by the method according to claim 6, and the microstructure of the alloy comprises the columnar grains of β-Ti and the equiaxed grains of β-Ti as matrix, the intragranular uniformly distributed spherical $(Ti, Zr)_2Si$ phase and the grain boundary discontinuously distributed $(Ti, Zr)_2Si$ phase as reinforcing phase, wherein the size of the β-Ti grains is 1-13 μm, and the size of the spherical $(Ti, Zr)_2Si$ phase grains is 50-300 nm; and the grain boundary discontinuously distributed $(Ti, Zr)_2Si$ phase is in a strip shape, with the width of 30-200 nm, and the aspect ratio of 1-6.

14. A Si-containing high-strength and low-modulus medical titanium alloy, characterized in that it is prepared by the method according to claim 7, and the microstructure of the alloy comprises the columnar grains of β-Ti and the equiaxed grains of β-Ti as matrix, the intragranular uniformly distributed spherical $(Ti, Zr)_2Si$ phase and the grain boundary discontinuously distributed $(Ti, Zr)_2Si$ phase as reinforcing phase, wherein the size of the β-Ti grains is 1-13 μm, and the size of the spherical $(Ti, Zr)_2Si$ phase grains is 50-300 nm; and the grain boundary discontinuously distributed $(Ti, Zr)_2Si$ phase is in a strip shape, with the width of 30-200 nm, and the aspect ratio of 1-6.

* * * * *